United States Patent [19]

Gallup et al.

[11] Patent Number: 5,435,308
[45] Date of Patent: Jul. 25, 1995

[54] MULTI-PURPOSE MULTI-PARAMETER CARDIAC CATHETER

[75] Inventors: David A. Gallup, Hayward; Timothy J. Hughes, Palo Alto; John Sperinde, Saratoga, all of Calif.

[73] Assignee: Abbott Laboratories, Abbott Park, Ill.

[21] Appl. No.: 914,279

[22] Filed: Jul. 16, 1992

[51] Int. Cl.$^6$ ............................................. A61B 5/028
[52] U.S. Cl. .................................. 128/634; 128/692; 128/713; 128/736
[58] Field of Search ................ 128/691, 634, 713, 736, 128/664–665, 666–667, 692, 633

[56] References Cited

U.S. PATENT DOCUMENTS

| | | | |
|---|---|---|---|
| 4,217,910 | 8/1980 | Khalil | 128/670 |
| 4,776,340 | 10/1988 | Moran et al. | 128/634 |
| 4,785,823 | 11/1988 | Eggers et al. | 128/692 |
| 4,941,475 | 7/1990 | Williams et al. | 128/692 |

*Primary Examiner*—Angela D. Sykes
*Attorney, Agent, or Firm*—Robert E. Wexler; Harry G. Thibault

[57] ABSTRACT

A multi-lumen, multi-purpose cardiac catheter which incorporates optical filaments and an optical coupler for use with external apparatus for determining the oxygen concentration in the blood of a patient under critical care conditions, as well as incorporating therein a heater coil useable with a second external apparatus for measurement of continuous cardiac output. The catheter also includes a thermistor and at least one injectate port for enabling the user to also conduct thermal dilution readings and obtain intermittent measurements of cardiac output. The combination of a thermal dilution catheter with a SVO$_2$ catheter and a continuous cardiac output catheter gives the multi-purpose catheter above described substantial versatility as well as providing the user with a versatile cardiac catheter device which enables him to conduct multiple evaluations of disparate blood-related parameters which require the use of separate apparatus. Simply by switching from one external apparatus to the other, the user can obtain readings for different blood-related parameters useful in the treatment of the cardiac patient.

20 Claims, 7 Drawing Sheets

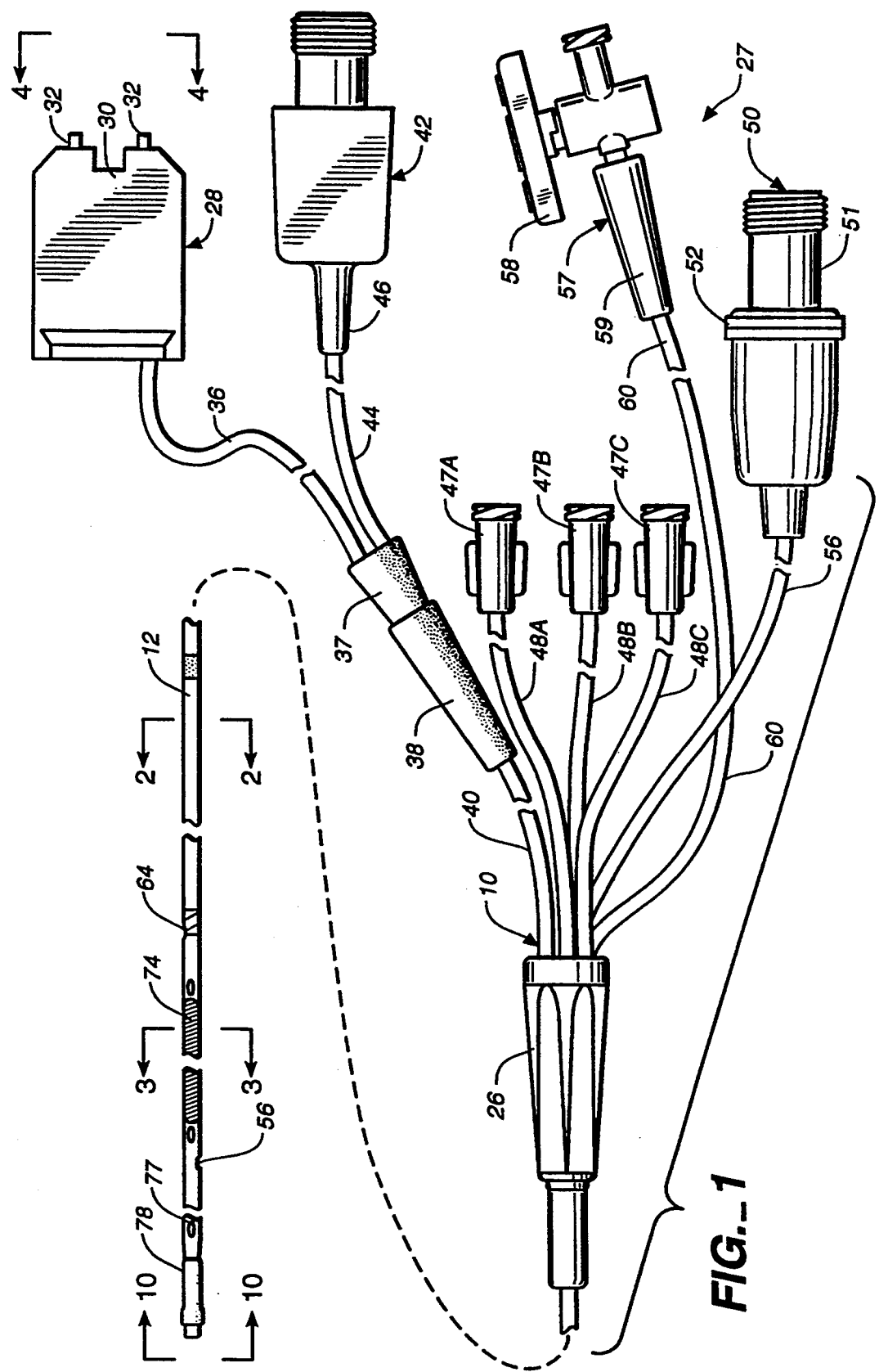
FIG._1

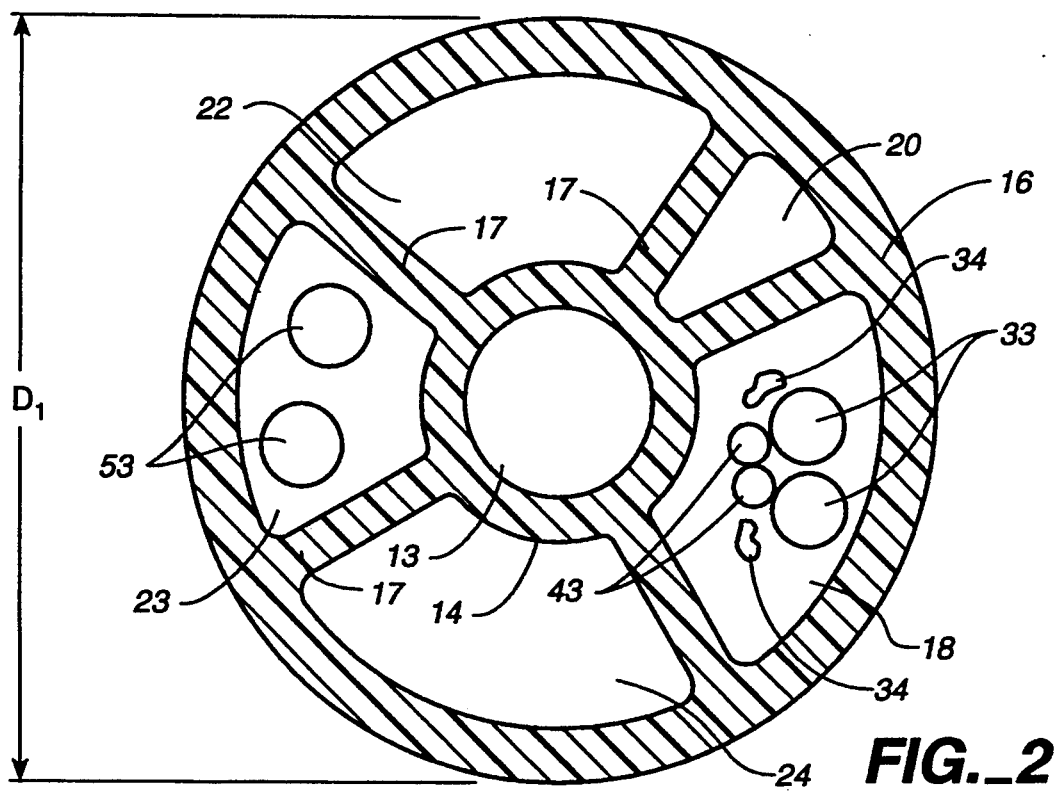
FIG._2
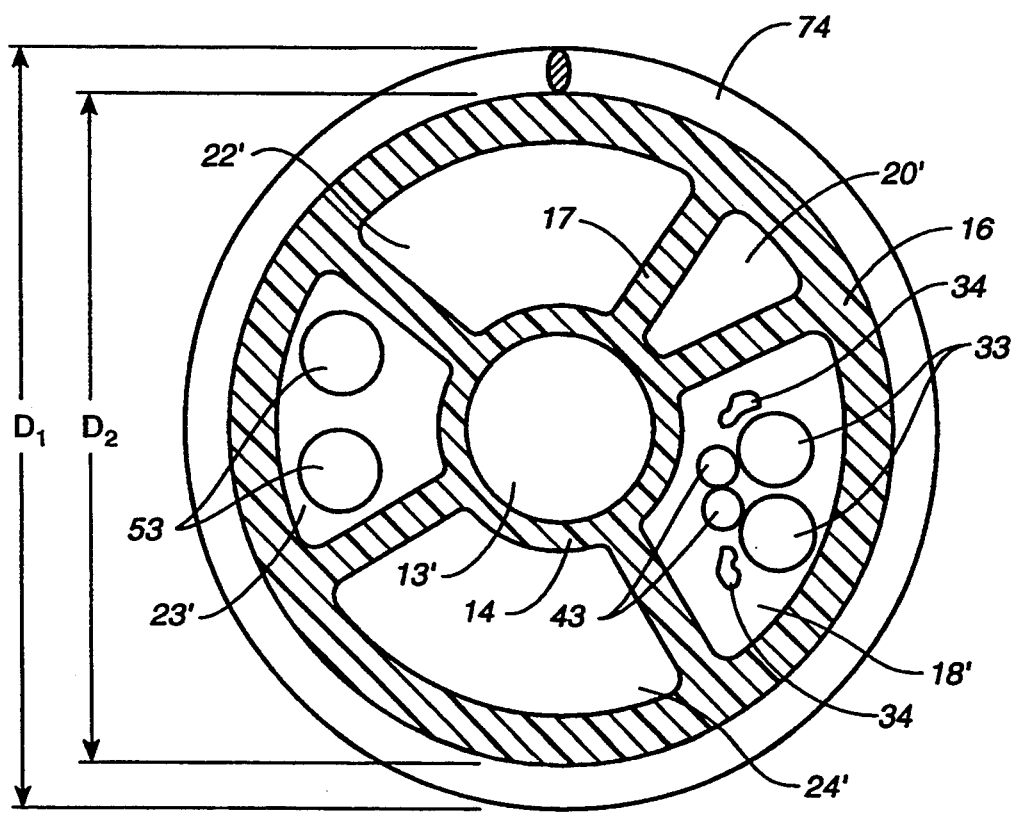
FIG._3

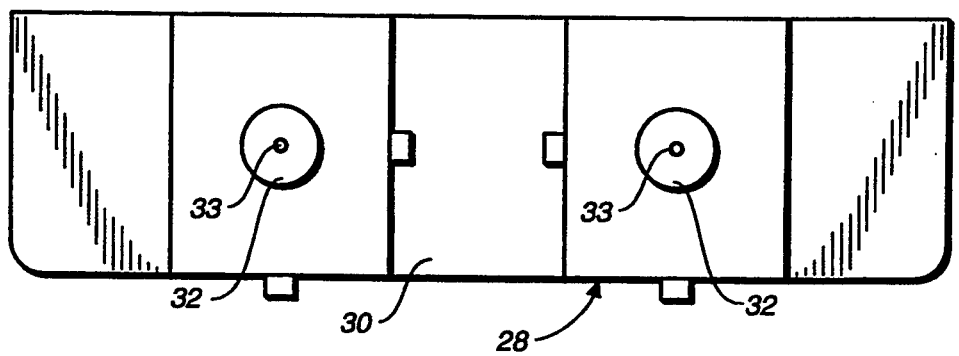
FIG._4
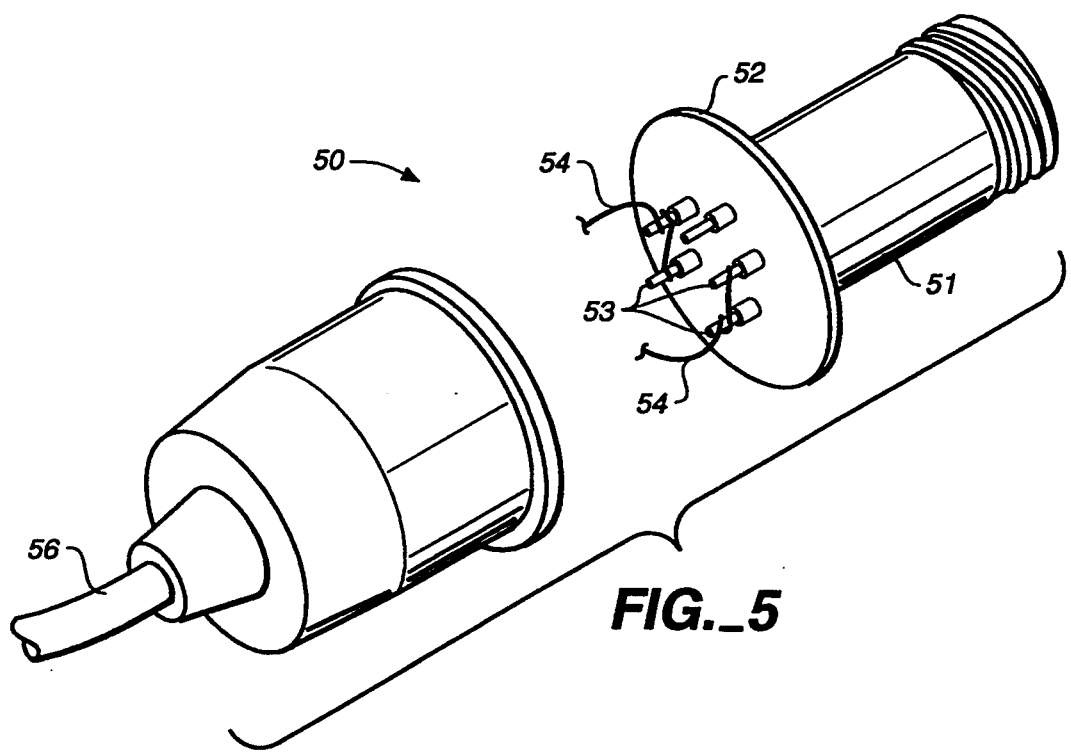
FIG._5

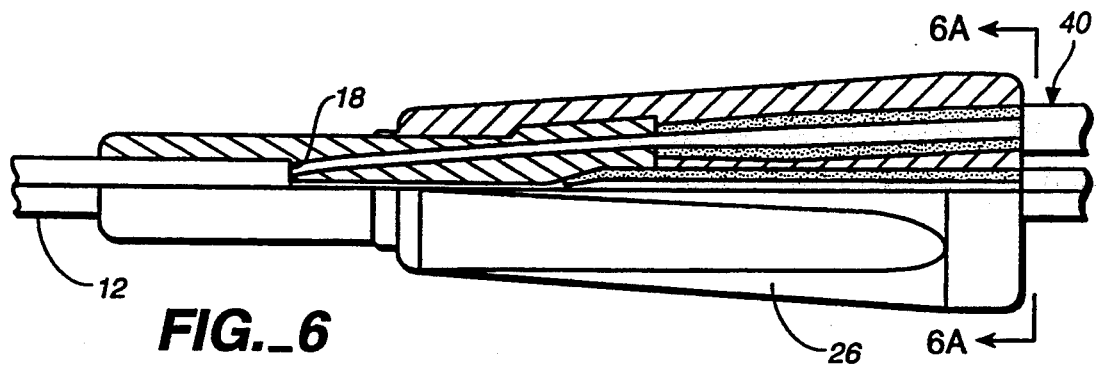
FIG._6
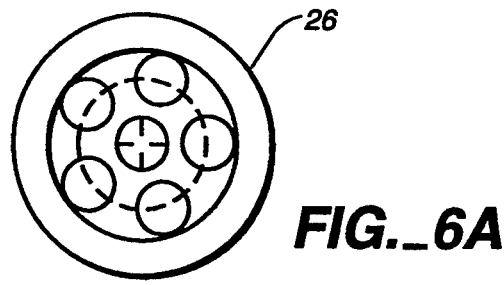
FIG._6A
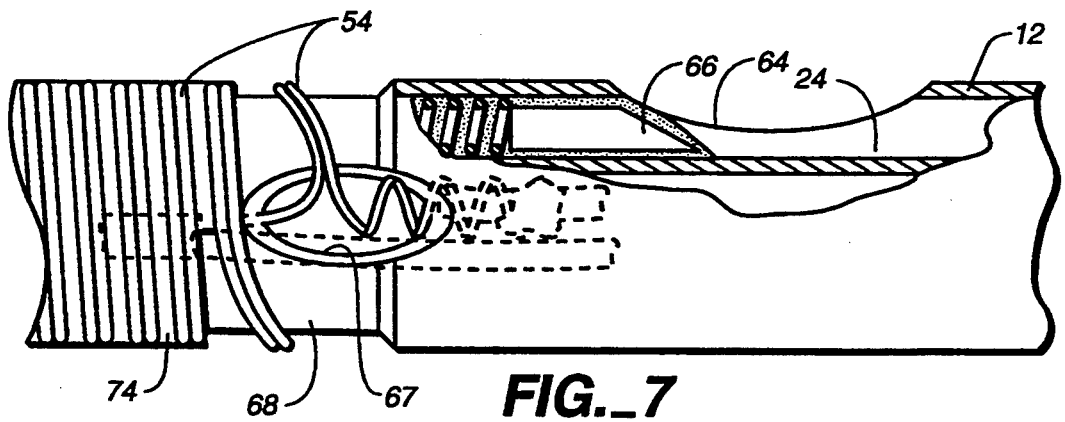
FIG._7
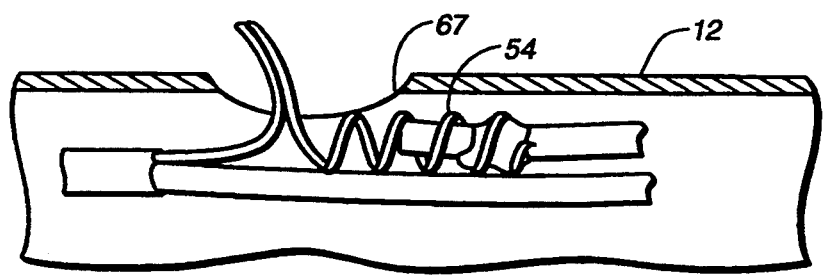
FIG._7A

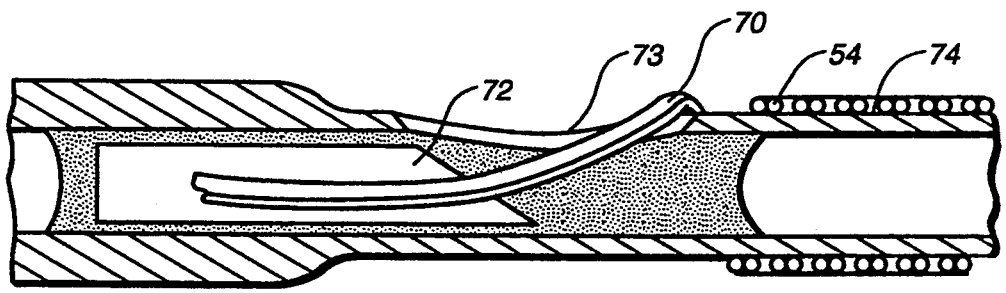
FIG._8
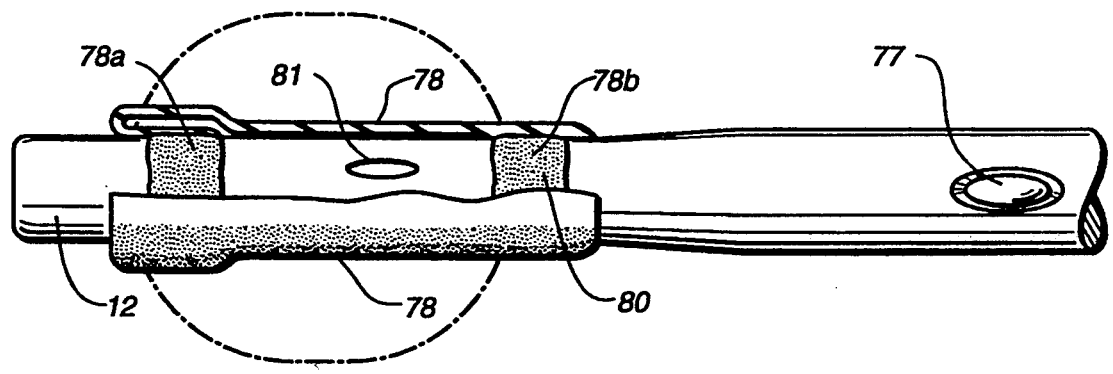
FIG._9
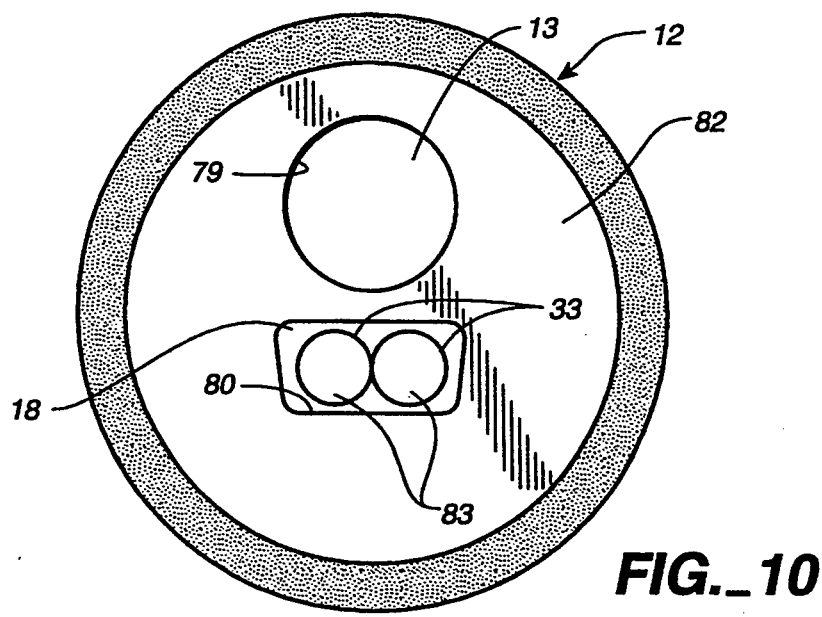
FIG._10

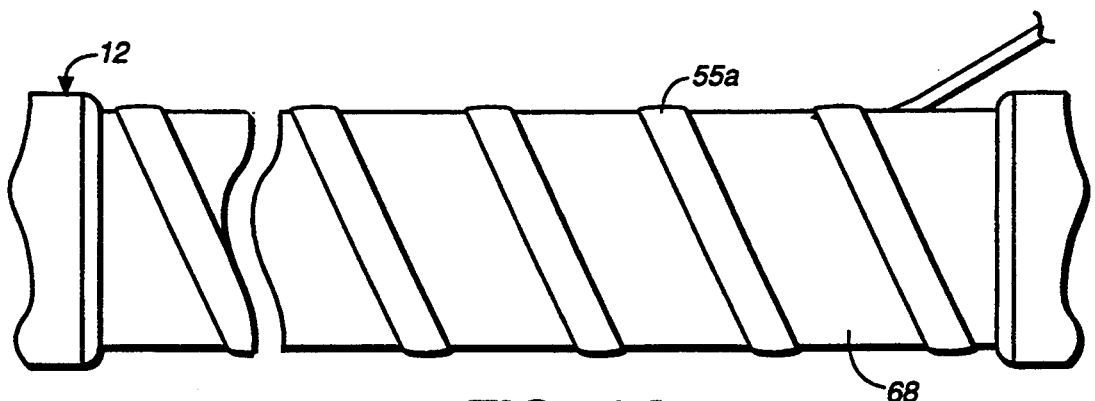
FIG._8A
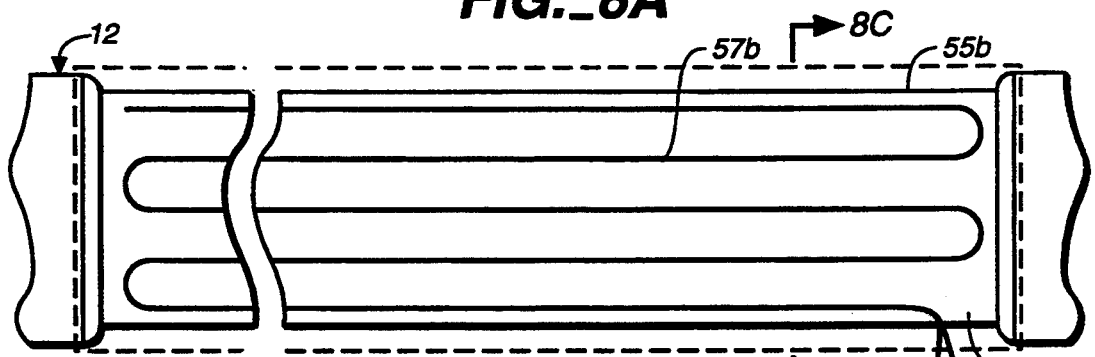
FIG._8B
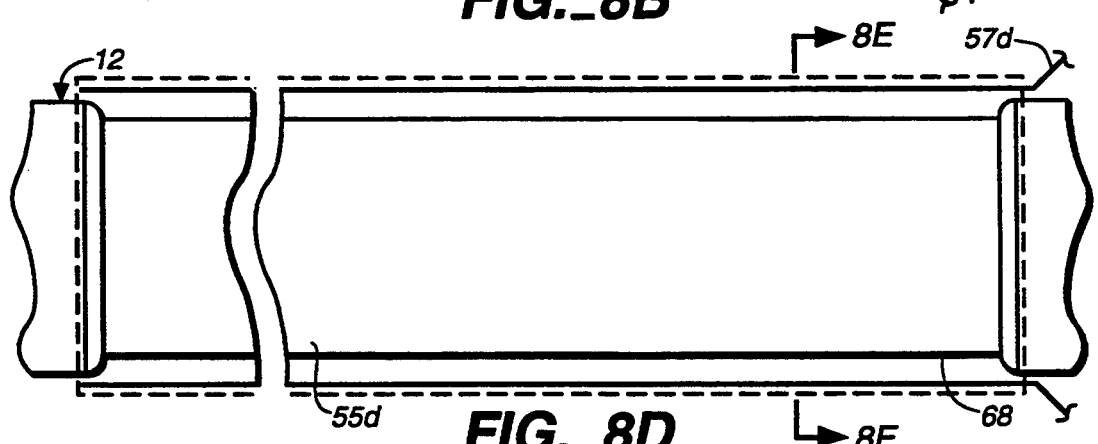
FIG._8D
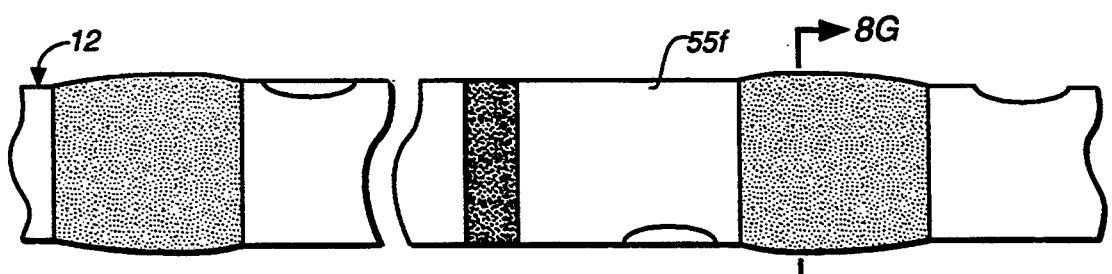
FIG._8F

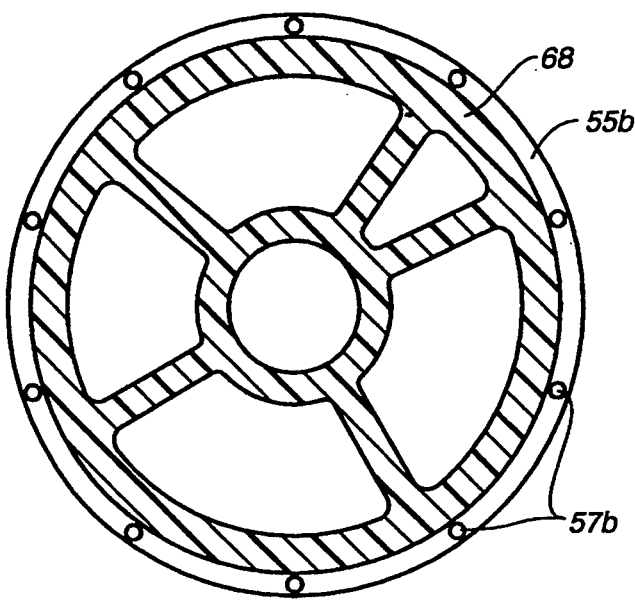
FIG._8C
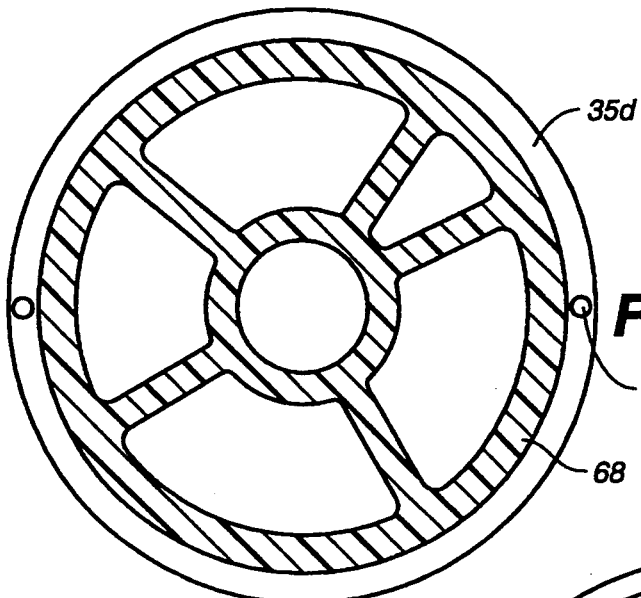
FIG._8E
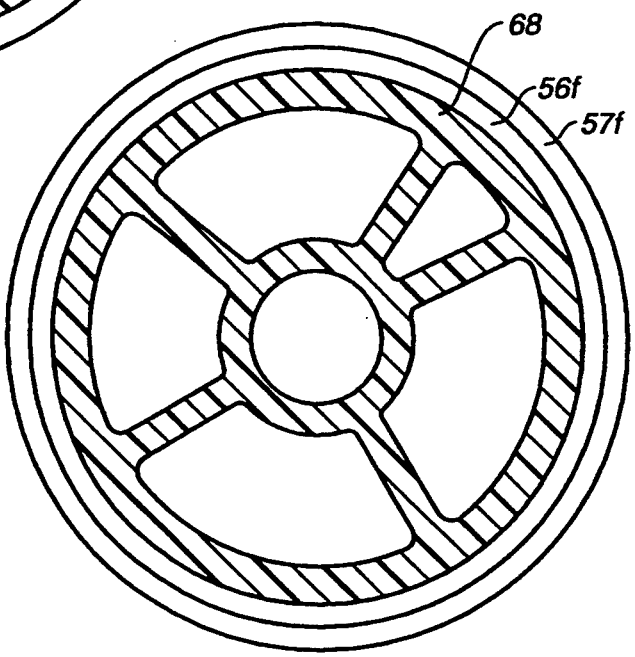
FIG._8G

MULTI-PURPOSE MULTI-PARAMETER CARDIAC CATHETER

BACKGROUND OF THE INVENTION

1. Field of the Invention

The present invention relates to multi-purpose catheters and in particular, to multi-purpose multi-parameter cardiac catheters having multiple lumens and useable separately to perform diverse independent procedures including oximetry, thermal dilution and continuous cardiac output to obtain significantly useful blood parameters, such as oxygen saturation values ($SvO_2$), thermal dilution values and continuous cardiac output values.

2. History of the Prior Art

Multi-lumen cardiac catheters are known. Further, it is known to provide within a multi-lumen catheter a plurality of optical fibers, such optical fibers used in conjunction with a signal processing apparatus to measure the oxygen concentration ($SVO_2$) in the blood.

Thermal dilution catheters have been provided for the measurement of the temperature of mixed fluids in the blood and veins in order to provide important diagnostic information. Exemplary of the patent art relating to such catheters is the patent of H. Khalil, U.S. Pat. No. 4,217,910 and the patents and literature referred to therein.

Thermal dilution is the application of the calorimetric principle that, in a mixture of fluids of different temperatures, the heat lost by one fluid equals the heat gained by the other. For each fluid the mathematical product of the temperature change, specific heat and mass is equal.

The recognized method for the study of blood circulation involves producing a temperature change in the blood at one point in the blood flow and measuring the temperatures change at a second point downstream of the first one. Assuming that the measurement of the temperature change occurs at a point downstream of the heat source, and that the heat content of the blood is uniform, the measured change will reflect the amount of blood passing through the blood vessel. Thus, thermal dilution techniques can provide an intermittent measure of cardiac output.

It is also known to provide an injectateless method of measuring cardiac output in which a small heater or cooler is incorporated into the catheter to generate a temperature change which is measured downstream of the heat source, in a manner similar to the introduction of an injectate into the blood stream through the thermal dilution method, such injectateless method to provide a continuous measure of cardiac output.

Each technique described above provides an important function in determining certain critical parameters associated with the treatment of a critically ill patient. However, the methods described to obtain such parameters are diverse, not necessarily compatible, and to date, unable to be obtained through the use of a single cardiac catheter device.

However, it would be desirable to combine within a single catheter the diverse mechanisms required to monitor not only the oxygen concentration in the blood, but also continuous cardiac output and further to provide within the same catheter a method for conducting thermal dilution measurements.

SUMMARY OF THE INVENTION

Accordingly, in the present invention, is devised a multi-purpose, multi-parameter cardiac catheter which incorporates fiber optic technology so as to measure oxygen concentration ($SVO_2$) in the blood, as well as incorporates in such catheter means for conducting a continuous cardiac output evaluation for the patient. The multi-purpose, multi-parameter cardiac catheter of the present invention also includes injectate ports compatible with a thermal dilution technique to provide intermittent cardiac output measurements from the same catheter.

In accordance with the present invention, the multi-purpose multi-parameter cardiac catheter comprises a pulmonary artery multi-lumen catheter wherein certain of the lumens receive fiber optic filaments which extend through the catheter to provide a fiber optic interface in the blood stream of the patient at the distal end of the catheter, as well as a fiber optic electronic interface at the proximal end to the catheter connectable to a monitor for reading and monitoring oxygen concentration in the blood.

Adjacent to the distal end of the catheter is installed a fast response thermal element compatible with and operative with appropriate signal processing apparatus to provide continuous cardiac output monitoring capability. In the preferred embodiment of the present invention, the thermal element is mounted at a necked down portion of the catheter body. A thermistor provided downstream of the thermal element can also be used in conjunction with an injectate port provided in one of the lumens of the catheter to enable such catheter to also be used in conducting thermal dilution measurements, such thermal dilution measurements provided as intermittent measurements of cardiac output to support or replace the readings taken through the catheter under continuous cardiac output monitoring.

Thus, the multi-purpose, multi-parameter cardiac catheter of the present invention enables the user to conduct a variety of monitoring techniques which measure and monitor significant blood-related parameters useful in the treatment of the critically ill cardiac patient. Moreover, the multi-purpose multi-parameter cardiac catheter of the present invention allows such disparate techniques to be conducted using the same catheter, thus enabling the caregiver to monitor multiple parameters at a single catheter location. Moreover, the multi-purpose multi-parameter cardiac catheter of the present invention further incorporates therein apparatus for performing thermal dilution measurements, thus to provide a secondary measurement of cardiac output to compare with the continuous cardiac measurements or to substitute therefor as needed.

Because it is not known to provide such disparate techniques at a single catheter location, the multi-purpose cardiac catheter of the present invention thus provides substantial advantages over known single purpose catheters and substantially advances the ability of the caregiver to treat a critical ill patient and further to limit the number of invasive procedures associated with such treatment.

These and other advantages will be more fully understood when the present invention is described in detail below, particularly when such description is considered in conjunction with the accompanying drawings.

BRIEF DESCRIPTION OF THE DRAWINGS

FIG. 1 is a side elevational view of the multi-purpose, multi-parameter cardiac catheter of the present invention, the catheter being shown with broken lines to display all the significant features of the catheter from its distal end to its proximal end;

FIG. 2 is an enlarged cross-sectional view taken along the lines 2—2 of FIG. 1;

FIG. 3 is an enlarged cross-sectional view taken along lines 3—3 of FIG. 1;

FIG. 4 is an enlarged plan view taken along lines 4—4 of FIG. 1;

FIG. 5 is an exploded perspective view of the heater plug of FIG. 1;

FIG. 6 is a side elevation, partially in section, of a manifold of the catheter of. FIG. 1;

FIG. 6A is an end view of FIG. 6 taken along lines 6A—6A of FIG. 6;

FIG. 7 is an enlarged view in partial section of a proximal notch provided near a proximal end of a thermal element and the distal end of the catheter;

FIG. 7A is a sectional view of the thermal element connection shown in FIG. 7;

FIG. 8 is an enlarged sectional view taken at the distal end of the thermal element at the distal end of the catheter;

FIG. 8A is a second alternative embodiment of the thermal element of the catheter of the present invention;

FIG. 8B is a third alternative embodiment of the thermal element of the catheter of the present invention;

FIG. 8C is an enlarged cross-sectional view, taken along the lines 8C—8C of FIG. 8B;

FIG. 8D is a fourth alternative embodiment of the thermal element of the catheter of the present invention;

FIG. 8E is an enlarged cross-sectional view, taken along the lines 8E—8E of FIG. 8D;

FIG. 8F is a fifth alternative embodiment of the thermal element of the catheter of the present invention;

FIG. 8G is an enlarged cross-sectional view, taken along the lines 8G—8G of FIG. 8F;

FIG. 9 is an enlarged side elevation in partial section of the distal end of the catheter; and FIG. 10 is an enlarged plan view of the distal end of the catheter, taken generally along the lines 10—10 of FIG. 1.

DETAILED DESCRIPTION

FIG. 1 is a perspective view of the multi-purpose, multi-parameter catheter 10 of the present invention. The main body 12 of the catheter 10 is an extended section of polyvinyl chloride (PVC) tubing. In the catheter 10 of the preferred embodiment, tubing 12, as shown in FIG. 2, is a complex multi-lumen tubing having a central lumen 13 defined by an interior PVC core 14 which is connected to a peripheral wall 16 of the tubing 12 by support ribs 17. Spaces between support ribs 17, the interior core 14 and the peripheral wall 16 define a series of interior longitudinal lumens in the catheter tubing 12. For example, in FIG. 2 can be seen optics, Kevlar and thermistor lumen 18, balloon lumen 20, distal thermal element pressure port lumen 22, thermal element connector lumen 23 and a proximal lumen 24.

Central or distal lumen 13, the optics lumen 18, the balloon lumen 20, the distal thermal element pressure port lumen 22, the thermal element connector lumen 23 and the proximal lumen 24 are generally parallel and coextensive for the entire working length of the catheter main body tubing 12, which in the preferred embodiment is 110 centimeters. Interposed between the catheter tubing 12 and catheter interconnects (discussed below) at the proximal end of the catheter 10 is a manifold 26 which will be described in greater detail below.

At the proximal end 27 of the catheter 10 is provided a series of interconnects between the catheter lumens, with the interface between said interconnects and the catheter lumens being provided in the manifold 26.

As seen in the upper right hand corner of FIG. 1, the first of the interconnects noted above is a fiber optic coupler 28. The coupler body 30 is a molded plastic body which plugs into an optical module associated with a $SVO_2$ monitor (not shown). At the proximal end of the coupler 28 are a pair of plug-in members 32 which receive fiber optic filaments 33 (also see FIG. 4). Included with the fiber optic filaments 33 are a series of elongated Kevlar elements 34 (FIG. 2) which support and protect the fiber optic filaments 33 in the connector 28, in connecting tubing 36 connected between the fiber optic coupler 28 and a secondary manifold 37 which is connected to a stop cock body 38 at a proximal end thereof with tubing 40 extending from the distal end of the stop cock body 38 and into the manifold 26 at its proximal end.

Similarly, a thermistor connector 42 includes a pair of thermistor wires 43 (FIG. 2) which extend through tubing 44 connected at the thermistor connector 42 by molded fitting 46 and are received into the secondary manifold 37 and stopcock 38 to be received into the tubing 40 connected to the manifold 26.

Next are a series of luer lock fittings 47, with each fitting 47 and its associated tubing 48 interfacing with a corresponding lumen of the catheter tubing 12 at the manifold 26. For convenience in use, in the preferred embodiment of the present invention the tubing 48 is color coded. Luer lock fitting 47a is connected to tubing section 48a, and tubing 48a is connected at its distal end to the pulmonary artery distal lumen 13 in the manifold 26. Next, the CVP luer lock 47b is connected to tubing section 48b which is in turn connected at its distal end to the proximal lumen 24 in the manifold 26. Next, luer lock fitting 47c is connected at its proximal end to tubing section 48c which is in turn connected at its distal end to the distal thermal element pressure port lumen 22 in the manifold 26.

Thermal element plug 50 comprises a plastic body 51 having a cylindrical disc 52 joined thereto at a mid portion of the plug. The disc 52 a peripheral flange which extends beyond the body 51 of the plug 50. Mounted in the disc 52 are a plurality of metal pins 53 (FIG. 5) which extend through the plug 50 to protrude at an opposite end thereof. Connected to the lower end of the pins 53 are thermal element connectors or wires 54 which connect to the pins 53 that protrude from the back of the disc 52 to be received into extension tubing 56 which is connected between the thermal plug 50 and the manifold 26. The thermal element connectors can be heater wires 54 as in the preferred embodiment of FIG. 1, or could be replaced by coils carrying temperature regulated fluid therein as described in greater detail below. The thermal element connectors 54 continue through the manifold 26 into the thermal element connector lumen 23 to extend along the working length of the catheter tubing 12 to a thermal element 55, disposed near the distal end of the catheter 10.

Stop cock 57 which includes stop cock valve 58, stop cock sleeve 59 and extension tubing 60 interfaces with the balloon lumen 20 at the manifold 26.

In FIG. 6, the manifold 26 is shown partly in section. Not all lumen/tubing interfaces in the manifold 26 are shown in FIG. 6, but sufficient detail is provided in FIG. 6 to give an understanding of the construction within the interior of the manifold 26.

Within the manifold 26, each extension tube is aligned and abutted with its respective lumen of the catheter 10 at the interface thereof, the manifold 26 fixing the position of the main body tubing 12 of the catheter 10 with respect to the extension tubing. Although only the tubing 40 connected to the optics lumen 18 is shown in section in FIG. 4, the drawing is illustrative to depict the manifold interface for each catheter lumen and its respective extension tubing section.

FIGS. 2 and 3 can now be reexamined to understand the interior workings of the catheter 10. For example, note in FIG. 2 that the optics, Kevlar and thermistor lumen 18 includes not only optical fiber filaments 33 but also the supporting Kevlar filaments 34, as well as thermistor wires 43. Opposite lumen 18 is the thermal element lumen 23 which receives therein thermal element connectors 54. Note that FIG. 3 is taken looking toward the distal end of the catheter 10 and is taken about 25 centimeters from that distal end. Although the 110 centimeter length of the catheter tubing 12 is referred to as the working length, for about 85 centimeters the main body tubing 12 is essentially smooth. In the 25 centimeters of main body tubing 12 beginning at the distal end and moving forward are located many of the apparatus associated with the detection of blood-related parameters through the use of the catheter 10.

About twenty-five centimeters from the distal end of the catheter 10 is located a proximal notch 64 (FIG. 7) provided in the proximal lumen 24. As can be seen from the enlarged view of FIG. 7, the proximal lumen 24 is plugged by a solid PVC plug 66 to direct the flow of injectate into the blood stream rather than permitting it to advance in the proximal lumen 24 beyond the proximal notch 64.

About one centimeter from the proximal notch 64, the thermal element connectors 54 emerge from the thermal element connector lumen 23 at a notch 67 (FIG. 7A). In the preferred embodiment of the present invention connector 54 comprise bifilar heater wires which emerge from the lumen 23 at notch 67 to be thereafter circumferentially wound about the catheter main body 12 at a reduced diameter section 68 to form a thermal element or heater coil 55 about 10 centimeters long.

Such reduced diameter section 68 is also depicted in FIG. 3. Note in the reduced diameter portion 68 of catheter 10 shown in FIG. 3 that although the diameter of the tubing 68 is reduced from diameter $D_1$ to diameter $D_2$, and that all lumens, including the optics, Kevlar and thermistor lumen 18', the balloon lumen 20', the distal thermal element pressure port lumen 22', the thermal element connector lumen 23' and the proximal lumen 24' are reduced in size, such lumens remain sufficiently large to receive and support the fiber optic filaments 33, the Kevlar filaments 34 and the thermistor wires 43 in reduced diameter section lumen 18' and the thermal element connectors 54 in reduced diameter section lumen 23'.

Although the preferred embodiment of the present invention discloses a multi-lumen multi-purpose catheter having a reduced-diameter portion of the catheter body for receiving a thermal element, it is believed that the incorporation of a reduced-diameter portion in the catheter body is not essential to the practice of the present invention. For example, thermal element 55 could be mounted at the distal end of a fiber optic catheter having a catheter body of uniform cross-section at a location comparable to the reduced-diameter portion 68 and continue to provide many of the advantages ascribed to the multi-lumen, multi-purpose catheter of the preferred embodiment of the present invention.

In the preferred embodiment, the opening 67 is potted to cover the wire 54. The wire 54 is of a bifilar configuration and of a soft copper composition and is circumferentially wound about the reduced diameter portion 68 of the catheter body 12 for about 10 centimeters and terminates at a second notch 70 in the heater wire lumen 23. The terminus of the heater wires 54 is best seen in FIG. 8 in which the wires 54 are soldered to a solid PC rod 72. FIGS. 7 and 8 also show the pitch or spacing of the wires 54 to be 0.017" center to center. The notch 70 is also potted to enclose the wires 53 with a polyurethane coating 73. As can also been seen in FIGS. 1, 3 and 7, a polyurethane coating 74 overlies the wires 54 for the entire length of the heater coil 55.

Alternative embodiments of the thermal element 55 are shown in FIGS. 8A through 8G.

In FIG. 8A, a second embodiment of the thermal element 55 comprises thin film member 55a, which is spiral wound about the reduced-diameter section 68 of the catheter body 12.

In FIG. 8B, a third embodiment of the thermal element 55 comprises thin film sleeve 55b, incorporating a coiled conductive element 57b embedded therein in the coiled pattern shown, which overlies the reduced-diameter portion 68 of the catheter body 12.

The relationship between the sleeve 55b and the catheter body 12 at reduced-diameter portion 68 is better seen in the enlarged cross-sectional view of FIG. 8C.

In FIG. 8D, a fourth embodiment of the thermal element 55 comprises a self-regulating conductive plastic sleeve 55d, incorporating power wires 57d, on opposite sides thereof as shown in FIG. 8E, mounted on the reduced-diameter section 68 of the catheter body 12.

In FIGS. 8F and 8G, a fifth embodiment of the thermal element 55 comprises a heat exchanger 55f, having an interior fluid-filled jacket 56f, an exterior sheath 57f, and coils (not shown) comparable to connectors 54 associated therewith, to transfer thermally regulated fluids from an external heat exchanger (not shown) to heat exchanger 55f.

In each instance, each thermal element 55a–55f is connected to an appropriate thermal regulator or heater exchanger (not shown) by thermal wires or coils 54 extending from the thermal element 55 to an appropriate connector, comparable to thermal plug 51, disposed at the proximal end of the catheter 10.

About one centimeter from the distal end of the heater coil 55 is a distal thermal pressure port 76 (FIG. 1). The distal thermal pressure port 76 is very similar to the proximal notch 64 and the structural details of the proximal notch 64 as shown in FIG. 7 apply equally to the pressure port 76.

About 7 centimeters from the pressure port 76 is the distal end 77 of thermistor 42. Distal end 77 of thermistor 72 is exposed to the blood stream and senses the temperature therein.

Now refer to the distal end of the catheter body 12 in both FIGS. 1 and 9. As better seen in FIG. 9 the distal end of the catheter body 12 shows a balloon 78 secured to the catheter body 12 at opposite ends 78a and 78b by adhesive 80. The balloon 78 is attached to the periphery of the catheter body 12 and is inflated through the balloon lumen 20 at an opening 81 which opens into the balloon lumen 20 at the distal end of the catheter 10. The balloon 78 is inflated by a means well known in the art.

The distal end of the catheter as seen in FIG. 10 includes an open port 79 which is the exit port 79 for the distal lumen 13 and a closed port 80 which is the distal port 80 for the optics, Kevlar and transistor lumen 18. Exposed at the distal end 82 of the catheter body 12 are the ends 83 of optical fibers 33.

Thus, by design the catheter 10 of the present invention incorporates thermal element 55 at a reduced diameter portion of the catheter body 12 coil for use in the measurement of continuous cardiac output measurement, such measurement taken in conjunction with the thermistor 77 located distally of the thermal element 55. For a complete description of the use of such thermal element in an application for measurement of continuous cardiac output, please refer to U.S. application Ser. No. 07/717,549 entitled "Heated Catheter for Monitoring Cardiac Output" and filed Jun. 19, 1991 and assigned to the assignee of the present invention.

The incorporation of the heater coil 55 into the catheter body 12 for the measurement of continuous cardiac output is achieved with no loss in the capability of the catheter to provide a measurement of oxygen concentration or $SVO_2$ in the blood through the use of fiber optics as described in U.S. Pat. No. 4,453,218 entitled "Signal Filter Method and Apparatus" and assigned to the assignee of the present invention.

Such dual capacity is permitted by the provision of a reduced diameter body portion of the catheter body 12 which reduces not only the diameter of the catheter body at such body portion but also reduces the size of the lumens in which the optics, as well as the heater wires are located. However, such reduction in lumen size is not adverse to fiber optic performance as it relates to measurement of $SVO_2$ or to thermistor performance as it relates to the measurement of temperature. Further, the reduced diameter portion of the catheter 10 has no impact on the efficacy of the thermal element connectors 54 used in the thermal element 55. Nor does the reduced diameter catheter body portion have any effect on the flow of injectates through the flow ports or the removal of samples through those ports.

Simply stated, the reduced diameter portion 68 of the catheter body 12 has no impact on the measurements to be taken by the catheter 10 in connection with the evaluation of separate blood-related parameters associated with oxygen saturation, continuous cardiac output and thermal dilution values. By mounting the thermal element 55 at the reduced diameter portion 68 the catheter 10 is useable for continuous cardiac output measurements and has a symmetric diameter for its entire working length. An alternative construction, such as a catheter body of a single diameter throughout its working length, which then wound a heater coil about the distal end thereof would produce a discontinuity in such catheter and such discontinuity could be noticeable in the insertion and removal of such catheter. The multi-purpose, multi-parameter cardiac catheter of the present invention incorporates the heater coil at a reduced diameter section thereof at the distal end of the catheter and yet generally maintains a single diameter throughout the working length of the catheter, because the addition of heater coil and coating at the reduced diameter portion creates an overall diameter at that portion that is consistent with the diameter at the remainder of the working length of the catheter. Consistency of diametric proportions throughout the working length of the catheter should facilitate insertion and removal of the catheter of the preferred embodiment of the present invention.

Having described a preferred embodiment of the present invention, it is not the intention to thereby limit the scope of the invention to the description set forth, but rather to define the invention in terms of the claims which follow.

We claim:

1. A multi-lumen multi-purpose cardiac catheter comprising a multi-lumen main body portion, a plurality of extension tubes, each connected to a respective lumen of the multi-lumen catheter and a manifold providing an interface between the main body of the catheter and the extension tubes, said catheter comprising:

a fiber optic apparatus associated with the catheter including optical filaments disposed in a fiber optic lumen and extending the working length of the main body of the catheter, and into a fiber optic coupler associated with the catheter;

temperature measurement apparatus mounted at a distal end of the catheter, wiring extending the working length of the catheter and into a housing associated with the catheter;

a necked down portion of the main body portion of the catheter, said necked-down portion 10–15 centimeters in length and disposed not less than 10–15 centimeters from the distal end of the catheter;

an external longitudinal thermal element disposed in the necked-down portion of the catheter; said thermal element comprising a heater coil wound about said necked down portion, said heater coil wound about the catheter and pitched at a center-to-center spacing sufficient to separate adjacent coils, connectors extending from the thermal element along the working length of the catheter to be connected to a thermal element housing at a proximal end of the catheter;

at least one lumen for holding and supporting fiber optic filaments;

at least one lumen for receiving thermal element connectors;

at least one lumen for receiving a device for temperature measurement;

at least one lumen associated with a balloon mounted at the distal end of the catheter for assisting in placement of the catheter in a patient;

a distal thermal pressure port disposed between the distal end of the heater coil and the distal end of the catheter; and catheter positioning apparatus comprising a balloon mounted at the distal end of the catheter, a balloon lumen extending from the balloon along the working length of the main body portion of the catheter to a device providing access to the balloon;

wherein the temperature measurement apparatus is operative with an external apparatus to provide a measurement of continuous cardiac output and, alternatively, the fiber optic apparatus is cooperative with external apparatus for providing a measurement of oxygen concentration in blood (SVO$_2$).

2. The multi-lumen, multi-purpose cardiac catheter of claim 1, wherein the heater coil windings have a center-to-center spacing in a range of 0.1 to 0.2 inches.

3. The multi-lumen, multi-purpose cardiac catheter as claimed in claim 1, wherein the temperature measurement apparatus comprises a thermistor which is at least 10 centimeters downstream of the distal end of the heater coil.

4. The multi-lumen, multi-purpose cardiac catheter as claimed in claim 3, wherein the heater coil is coated with a material structurally similar to the main body of the catheter.

5. The multi-lumen, multi-purpose cardiac catheter as claimed in claim 4, wherein the heater coil and the coating thereof mounted in the necked down portion of the catheter generally approximate the diameter of the main body portion of the catheter, thereby to effect a smooth insertion of the catheter into the body of the patient.

6. A multi-lumen, multi-purpose cardiac catheter as claimed in claim 5, wherein at least one lumen of the catheter comprises an injectate lumen having at least one injectate port provided upstream of the thermistor, thereby to enable injection of an injectate fluid into the blood stream of the patient to obtain thermal dilution readings at the thermistor to provide values for use in calculating intermittent cardiac output values.

7. The multi-lumen, multi-purpose cardiac catheter of claim 1, wherein the thermal element comprises a thin film member spirally wound about the catheter body near the distal end thereof.

8. The multi-lumen, multi-purpose cardiac catheter of claim 1, wherein the thermal element comprises a thin film sleeve having a single wire circuit embedded therein and overlying the catheter body near the distal end thereof.

9. The multi-lumen, multi-purpose cardiac catheter of claim 1, wherein the thermal element comprises a self-regulating conductive plastic sheath overlying the catheter body near the distal end thereof.

10. The multi-lumen, multi-purpose cardiac catheter of claim 1, when the thermal element comprises a heat exchanger having an interior fluid jacket disposed next to the catheter body near the distal end thereof, with an exterior sheath overlying said fluid jacket.

11. A multi-lumen multi-purpose cardiac catheter comprising a multi-lumen main body portion, a plurality of extension tubes, each connected to a respective lumen of the multi-lumen catheter and a manifold providing an interface between the main body of the catheter and the extension tubes, said catheter comprising:

a fiber optic apparatus associated with the catheter including optical filaments disposed in a fiber optic lumen and extending the working length of the main body of the catheter, and into a fiber optic coupler associated with the catheter;

temperature measurement apparatus mounted at the distal end of the catheter, wiring extending the working length of the catheter and into a housing associated with the catheter;

a necked down portion of the main body portion of the catheter, said necked down portion disposed near the distal end of the catheter;

an external longitudinal thermal element disposed in the necked-down portion of the catheter, said thermal element generally flexible along the length thereof disposed in the necked-down portion of the catheter;

connectors extending from the thermal element along the working length of the catheter to be connected to a thermal element housing at the proximal end of the catheter;

at least one lumen for holding and supporting fiber optic filaments;

at least one lumen for receiving thermal element connectors;

at least one lumen for receiving a device for temperature measurement;

at least one lumen associated with a balloon mounted at the distal end of the catheter for assisting in placement of the catheter in a patient; and catheter positioning apparatus comprising the balloon mounted at the distal end of the catheter, the balloon lumen extending from the balloon along the working length of the main body portion of the catheter to a device providing access to the balloon;

wherein the catheter includes a distal thermal pressure port disposed between the distal end of the thermal element and the distal end of the catheter and the thermal element is deliverable to an operative position in the pulmonary artery of a patient, and, in such position the thermal element is operative with an external apparatus to provide a measurement of continuous cardiac output and the fiber optic elements are operative with external apparatus to provide a measurement of oxygen concentration in blood (SVO$_2$).

12. The multi-lumen, multi-purpose cardiac catheter as claimed in claim 11, wherein the temperature measurement apparatus comprises a thermistor which is at least 10 centimeters downstream of the distal end of the thermal element.

13. The multi-lumen, multi-purpose cardiac catheter as claimed in claim 12, wherein the thermal element is coated with a material structurally similar to the main body of the catheter.

14. The multi-lumen, multi-purpose cardiac catheter as claimed in claim 13, wherein the thermal element and the coating thereof mounted in the necked down portion of the catheter generally approximate the diameter of the main body portion of the catheter, thereby to effect a smooth insertion of the catheter into the body of the patient.

15. A multi-lumen, multi-purpose cardiac catheter as claimed in claim 14, wherein at least one lumen of the catheter comprises an injectate lumen having at least one injectate port provided upstream of the thermistor, thereby to enable injection of an injectate fluid into the blood stream of the patient to obtain thermal dilution readings at the thermistor to provide values for use in calculating intermittent cardiac output values.

16. A multi-lumen multi-purpose cardiac catheter comprising a multi-lumen main body portion, a plurality of extension tubes, each connected to a respective lumen of the multi-lumen catheter and a manifold providing an interface between the main body of the catheter and the extension tubes, said catheter comprising:

a fiber optic apparatus associated with the catheter including optical filaments disposed in the fiber optic lumen and extending the working length of the main body of the catheter, and into a fiber optic coupler associated with the catheter;

temperature measurement apparatus mounted at the distal end of the catheter, wiring extending the working length of the catheter and into a housing associated with the catheter;

a necked down portion of the main body portion of the catheter, said necked-down portion of the catheter being 10–15 centimeters in length and disposed not less than 10–15 centimeters from the distal end of the catheter;

an external heater coil wound about the necked-down portion of the catheter near the distal end of the catheter the heater coil wound about the catheter being pitched at a center-to-center spacing sufficient to separate adjacent coils, to maintain flexibility of the catheter in said necked-down portion;

connectors extending from the heater coil along the working length of the catheter to be connected to a thermal element housing at the proximal end of the catheter;

at least one lumen for holding and supporting fiber optic filaments;

at least one lumen for receiving thermal element connectors;

at least one lumen for receiving a device for temperature measurement; and at least one lumen associated with a balloon mounted at the distal end of the catheter for assisting in placement of the catheter in a patient;

catheter positioning apparatus comprising the balloon mounted at the distal end of the catheter, the balloon lumen extending from the balloon along the working length of the main body portion of the catheter to a device providing access to the balloon;

wherein the catheter includes a distal thermal pressure port disposed between the distal end of the heater coil and the distal end of the catheter and the heater coil is operative with an external apparatus to provide a measurement of continuous cardiac output and the fiber optic elements are cooperative with external apparatus to provide a measurement of oxygen concentration in blood ($SVO_2$).

17. The multi-lumen, multi-purpose cardiac catheter as claimed in claim 16, wherein the temperature measurement apparatus comprises a thermistor which is at least 10 centimeters downstream of the distal end of the heater element.

18. The multi-lumen, multi-purpose cardiac catheter as claimed in claim 17, wherein the heater coil is coated with a material structurally similar to the main body of the catheter.

19. The multi-lumen, multi-purpose cardiac catheter as claimed in claim 18, wherein the heater coil and the coating thereof mounted in the necked down portion of the catheter generally approximate the diameter of the main body portion of the catheter, thereby to effect a smooth insertion of the catheter into the body of the patient.

20. A multi-lumen, multi-purpose cardiac catheter as claimed in claim 19, wherein at least one lumen of the catheter comprises an injectate lumen having at least one injectate port provided upstream of the thermistor, thereby to enable injection of an injectate fluid into the blood stream of the patient to obtain thermal dilution readings at the thermistor to provide values for use in calculating intermittent cardiac output values.

* * * * *